US010905316B2

(12) United States Patent
Waizenegger et al.

(10) Patent No.: US 10,905,316 B2
(45) Date of Patent: Feb. 2, 2021

(54) ENDOSCOPE AND METHOD FOR CENTRING AN EYEPIECE IN A MAIN UNIT OF AN ENDOSCOPE

(71) Applicant: Henke-Sass, Wolf GmbH, Tuttlingen (DE)

(72) Inventors: Markus Waizenegger, Muehlheim (DE); Daniel Seeh, Immendingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 454 days.

(21) Appl. No.: 15/711,367

(22) Filed: Sep. 21, 2017

(65) Prior Publication Data

US 2018/0078124 A1 Mar. 22, 2018

(30) Foreign Application Priority Data

Sep. 21, 2016 (DE) .................. 10 2016 117 805

(51) Int. Cl.
*A61B 1/00* (2006.01)
*G02B 23/24* (2006.01)

(52) U.S. Cl.
CPC ...... *A61B 1/00195* (2013.01); *G02B 23/2453* (2013.01)

(58) Field of Classification Search
CPC .............. A61B 1/00195; G02B 7/023; G02B 23/2407; G02B 23/2453; G02B 25/001
See application file for complete search history.

(56) References Cited

U.S. PATENT DOCUMENTS

| 3,936,143 | A | 2/1976 | Sato |
| 4,294,234 | A * | 10/1981 | Matsuo ............... A61B 1/07 385/117 |
| 4,440,157 | A | 4/1984 | Shishido |
| 6,363,193 | B1 | 3/2002 | Frische |
| 7,334,947 | B2 | 2/2008 | Rose et al. |
| 2014/0247333 | A1 | 9/2014 | Mizuno |

FOREIGN PATENT DOCUMENTS

| CH | 244866 A | 10/1946 |
| DE | 2358785 A1 | 6/1975 |
| DE | 29616666 U1 | 1/1997 |

* cited by examiner

*Primary Examiner* — Aaron B Fairchild
(74) *Attorney, Agent, or Firm* — Skaar Ulbrich Macari, P.A.

(57) ABSTRACT

An endoscope includes a main unit, which includes a centring bush with an inner surface which defines an axis of rotation; a first eccentric bush, which is mounted rotatable about the axis of rotation in the centring bush and comprises a first centring inner surface which defines a first rotation axis, wherein the first rotation axis is offset parallel to the axis of rotation by a first offset; a second eccentric bush which is mounted rotatable about the first rotation axis in the first eccentric bush and comprises a second centring inner surface which defines a second rotation axis, wherein the second rotation axis is offset parallel to the first rotation axis by a second offset; and an eyepiece, which is connected to the second eccentric bush and has an optical axis which is parallel to the second rotation axis.

16 Claims, 5 Drawing Sheets

ENDOSCOPE AND METHOD FOR CENTRING AN EYEPIECE IN A MAIN UNIT OF AN ENDOSCOPE

PRIORITY

This application claims the benefit of German Patent Application No. 102016117805.5, filed on Sep. 21, 2016, which is hereby incorporated herein by reference in its entirety.

FIELD

The present invention relates generally to an endoscope which comprises a main unit and an eyepiece. Furthermore, the invention relates to a method for centring an eyepiece in a main unit of an endoscope.

BACKGROUND

Endoscopes known from the state of the art comprise an objective lens and an eyepiece. The radiation collected by the objective lens is conveyed to the eyepiece via an optical guidance system, with the result that an object or a specimen can be viewed using the endoscope. The optical guidance system can be composed of several lenses which are centred with respect to each other. The objective lens, the plurality of lenses and the eyepiece each have an optical axis, which must be aligned with each other. Because of manufacturing tolerances, an adjustment system is necessary in order, for example, to adjust the optical axis of the eyepiece with respect to the optical axis of the lenses of the guidance system. Furthermore, because of temperature fluctuations, for example during autoclaving of the endoscope, the optical axis of the eyepiece can shift relative to the optical axis of the objective lens or of the lenses of the guidance system.

In the conventional state of the art, this adjustment system is realized by three adjusting screws which are arranged on the casing of a bush of a main unit of the endoscope. The eyepiece is received in the bush, with the result that the optical axis of the eyepiece can be shifted by screwing the corresponding adjusting screws in or out.

SUMMARY

An object of the invention to provide an endoscope in which the optical axis of the eyepiece can be adjusted reliably and quickly.

The object can be achieved by the endoscope according to the methods, apparatus, systems and devices described herein.

By way of example, the disclosure includes an endoscope which comprises a main unit, a first eccentric bush, a second eccentric bush and an eyepiece. The main unit comprises a proximal end and a centring bush at the proximal end. The centring bush comprises an inner surface, which defines an axis of rotation (or pivot axis). The first eccentric bush is mounted rotatable about the axis of rotation (or pivot axis) in the centring bush at the proximal end and comprises a first centring inner surface, which defines a first rotation axis, wherein the first rotation axis is offset parallel to the axis of rotation by a first offset. The second eccentric bush is mounted rotatable about the first rotation axis in the first eccentric bush and comprises a second centring inner surface, which defines a second rotation axis, wherein the second rotation axis is offset parallel to the first rotation axis by a second offset. The eyepiece is connected to the second eccentric bush and has an optical axis, which is parallel to the second rotation axis. The eyepiece can be displaced radially with respect to the axis of rotation by rotating the first eccentric bush and/or the second eccentric bush.

An advantage of certain embodiments is that the centring of the eyepiece, i.e. the shifting of the optical axis of the eyepiece parallel to the axis of rotation, can be achieved particularly simply in that the first eccentric bush and/or the second eccentric bush are rotated in the circumferential direction. Thus, no tools are necessary, as is required for example when adjusting the adjusting screws in the state of the art. Moreover, when the adjusting screws from the state of the art are used, there is the danger that the eyepiece can tilt i.e. that the optical axis of the eyepiece forms an angle relative to the optical axis of the lenses of the guidance system or the axis of rotation of the main unit, which can impair the imaging of the object. Because the first eccentric bush is rotatably mounted in the main unit and the second eccentric bush is rotatably mounted in the first eccentric bush the eyepiece cannot tilt when the first and/or second eccentric bush are rotated. Instead, this makes it possible for only a parallel offsetting of the optical axis of the eyepiece to occur. Tilting is ruled out in practice. A further advantage is that the adjustment of the eyepiece is particularly simple since there are only two parameters to be adjusted and not three, as in the case of the system of adjusting screws. Here, only the first eccentric bush and/or the second eccentric bush need to be rotated.

The adjustment of the optical axis of the eyepiece can be optionally effected in that the first eccentric bush comprises a first centring outer surface and the second eccentric bush comprises a second centring outer surface. The first centring outer surface abuts, for example, against the inner surface of the centring bush of the main unit and is thereby mounted rotatably in a form-fit manner, namely such that the first centring outer surface rotates about the axis of rotation of the centring bush. Because the first rotation axis of the first centring inner surface of the first eccentric bush is offset parallel to the axis of rotation by the first offset, the position of the first rotation axis can be altered by rotating the first eccentric bush. Because the first eccentric bush is mounted rotatable about the axis of rotation on the inner surface of the centring bush, the first rotation axis in particular does not tilt relative to the axis of rotation but is only offset in parallel. The first offset indicates the distance between the axis of rotation and the first rotation axis. The direction of the offset can be changed by rotating the first eccentric bush.

Since the second eccentric bush is mounted rotatable about the first rotation axis in the first eccentric bush, for example through the abutment of the second centring outer surface against the first centring inner surface, the second rotation axis is offset parallel to the first rotation axis by rotating the second eccentric bush about the first rotation axis; the reason for this is the second offset. The length of the second offset indicates the distance between the first rotation axis and the second rotation axis. The direction of the second offset can be adjusted by rotating the second eccentric bush. Because the eyepiece is connected to the second eccentric bush and thus the optical axis of the eyepiece is fixed relative to the second rotation axis, the optical axis of the eyepiece can be shifted in the radial direction of the second eccentric bush. The optical axis can coincide with the second rotation axis.

The optical axis of the eyepiece can be shifted parallel in a first direction by the first offset by rotating the first eccentric bush and the optical axis can be shifted in a second direction by the second offset by rotating the second eccentric bush. Since the first eccentric bush and the second eccentric bush are preferably rotatable through 360°, any desired direction can thus be set for the first and/or second offset. The maximum that the optical axis of the eyepiece can be shifted relative to the axis of rotation is thus the sum of the first offset and of the second offset. This is the case when the first offset and the second offset point in the same direction. Within a circle with a radius equal to the sum of the first offset and the second offset around the axis of rotation, the optical axis can adopt almost any position by rotating the first eccentric bush and the second eccentric bush.

The first offset can be understood in the mathematical sense as a first vector, which sticks out perpendicularly from the axis of rotation; it determines the radial direction of the first eccentric bush. The second offset can be understood in this sense as a second vector, which is arranged at the end point of the first vector. This results because the second vector emerges from the first rotation axis, which is arranged at the end point of the first vector. The direction of both vectors can be altered by rotating the first and/or second eccentric bush. The second rotation axis, and optionally the optical axis, is located at the end point of the second vector.

The endoscope can be constructed like an endoscope known from the state of the art and, in addition to the main unit, optionally comprises a shaft in which an objective lens and/or lenses of an optical guidance system are arranged. The objective lens is arranged in particular at a distal end of the endoscope.

At the proximal end, the main unit comprises the centring bush, which supports the first eccentric bush, the second eccentric bush and the eyepiece. The centring bush, the first eccentric bush, the second eccentric bush and the eyepiece together form an eyepiece centring mechanism for centring the eyepiece relative to the main unit. The centring bush comprises an inner surface which is circular in cross section perpendicular to the axis of rotation, for example, wherein the centre of the circle lies on the axis of rotation. In another embodiment, in cross section perpendicular to the axis of rotation, the inner surface is composed of circular segments, the radius of which has a centre which lies on the axis of rotation. The inner surface in particular defines a surface in which a cylinder is mounted rotatable about the axis of rotation. In an exemplary further development, the inner surface of the centring bush is the inner surface of a hollow cylinder in which, for example, one or more gaps extending in the direction of the axis of rotation are provided, wherein the axis of symmetry of the hollow cylinder corresponds to the axis of rotation.

The first eccentric bush is preferably mounted rotatable about at least the length of the first offset in the centring bush of the main unit. The rotatable mount can be formed as a slide bearing or roller bearing. As described above, the first eccentric bush optionally has a first centring outer surface which is circular in cross section perpendicular to the axis of rotation and/or the first rotation axis and has a centre which is offset parallel to the first rotation axis by the first offset. The first centring outer surface can also, in cross section perpendicular to the axis of rotation and/or the first rotation axis, be composed of several circular segments, the centre of which in each case is offset parallel to the first rotation axis. In particular, the centre of the first centring outer surface lies on the axis of rotation of the centring bush. The first centring outer surface is optionally designed in such a way that it is rotatably mounted in the centring bush like a cylinder. The axis of symmetry of this cylinder coincides with the axis of rotation and is offset with respect to the first rotation axis by the first offset.

The first centring inner surface can be designed analogously to the inner surface of the centring bush; in particular, the considerations set out in connection with the inner surface of the centring bush apply analogously to the first centring inner surface. The first centring inner surface can be arranged at the same axial height as the first centring outer surface or be offset from it axially.

The considerations set out with respect to the first eccentric bush preferably apply analogously to the variants and developments described for the second eccentric bush. Optionally, an area of the second eccentric bush by means of which the second eccentric bush is rotatably mounted in the first eccentric bush is at the same axial height as an area of the first eccentric bush by means of which the first eccentric bush is rotatably mounted in the centring bush.

The centring bush, the first eccentric bush and/or the second eccentric bush can be produced from metal, in particular from stainless steel. The axis of rotation, the first rotation axis, the second rotation axis and/or the optical axis can run parallel to each other.

The eyepiece can be permanently fixed to the second eccentric bush or attached to the second eccentric bush using securing means. For example, the eyepiece can be pushed into a cavity defined by the second centring inner surface and then fixed to the second eccentric bush. For adjustment, it is necessary for the optical axis of the eyepiece to have a firmly set distance relative to the second rotation axis, at least during the adjustment. The eyepiece can comprise one or more lenses which can be shifted, for example, relative to each other in order to alter the imaging properties of the eyepiece.

The endoscope can comprise a fixing device by means of which the position of the first eccentric bush relative to the centring bush, the position of the second eccentric bush relative to the first eccentric bush and/or the eyepiece relative to the second eccentric bush can be fixed before or after the adjustment. For example, screws can be provided which can be tightened to block a rotation of the first eccentric bush relative to the centring bush or the second eccentric bush.

The first and/or second eccentric bush can each comprise a centring section and a collar. The centring section optionally has the above-described properties, with the result that the offset of the optical axis relative to the axis of rotation can be adjusted with the respective centring section. The collar can be provided to fix the first eccentric bush and/or the second eccentric bush relative to each other or relative to the centring bush in the axial direction. For example, the collar can be a rim which protrudes from the centring section in the radial direction and serves as a limit stop in the axial direction.

A particularly simple design of the first eccentric bush and/or of the second eccentric bush can be achieved in that, in a further development, the first eccentric bush and/or the second eccentric bush in each case comprise a hollow cylinder with a compensating section, wherein the compensating section extends in the direction of the respective rotation axis and is alterable in its extent (that is transversely to the respective rotation axis) in order to alter the outer circumference of the hollow cylinder.

The centring section can in particular be formed as a hollow cylinder. The compensating section optionally extends along the entire axial length of the first and/or second eccentric bush. The compensating section makes it possible for the outer circumference of the first and second eccentric bush to be alterable, in particular in that the edges of the compensating section move towards each other to alter the outer circumference of the hollow cylinder, with the result that the circumference of the hollow cylinder is reduced. The compensating section can be produced, for example, from an elastic material, such as for example rubber. Through the provision of the compensating section, the first and/or second eccentric bushes have an area the circumference of which can be altered. In this way, the outer circumference of the first and/or second eccentric bush can be altered. This is useful for compensating for fluctuations in the circumference caused by temperature.

The offset can in particular be provided in that the thickness of the hollow cylinder changes in the circumferential direction. With the exception of the compensating section, this hollow cylinder comprises an inner surface which is circular in cross section with respect to the respective rotation axis and an outer surface which is circular in cross section with respect to the respective rotation axis, the centres of which are offset radially by the respective offset. The hollow cylinder thus has a wall thickness which is minimal in the direction of the offset and maximal on the opposite side. The wall thickness of the hollow cylinder changes from the minimum thickness to the maximum thickness along the circumference.

A variant of the compensating section which is particularly simple to produce is when the compensating section comprises a slot. For example, the compensating section is a slot extending axially in the first eccentric bush and/or the second eccentric bush. In this connection, by slot is meant that the first and/or second eccentric bush has a complete break in the circumferential direction and thus there is a gap in cross section in the circumferential direction. To alter the circumference, the ends lying opposite the slot can be moved away from each other or towards each other.

In order to simplify the adjustment, it is useful to know in which direction the first and/or second offset is arranged. A marking can be provided for this purpose. For example, the compensating section can be used as a marking. In a development, the marking is provided in that an imaginary extension in the direction of the first or second offset intersects the compensating section of the respective eccentric bush. The compensating section is thus the marking by means of which a user can identify in which direction the offset lies in the case of the first and/or second eccentric bush. The extension can be thought of as a straight line which connects the axis of rotation to the first rotation axis or the first rotation axis to the second rotation axis. This straight line intersects an area of the circumference of the first eccentric bush and/or of the second eccentric bush in which the compensating section, in particular the slot, is arranged. When the first eccentric bush and/or the second eccentric bush comprises a hollow cylinder, the compensating section thus lies in the area with the thickest wall thickness or the thinnest wall thickness.

In one development, it is preferred that the first offset is equal to the second offset. This means in particular that the length of the first offset is equal to the length of the second offset. If the first eccentric bush and the second eccentric bush are rotated such that the directions of the offsets are mirror-inverted, then the optical axis of the eyepiece lies on the axis of rotation of the centring bush since the two offsets cancel each other out. In this embodiment, it is therefore possible to provide a zero offset particularly simply.

In order to fix the current position of the optical axis relative to the axis of rotation it is provided in a development that a diameter of the inner surface of the centring bush can be reduced by the fixing device for holding in place by means of frictional connection. The fixing device is thus capable of deforming the centring bush radially inwards. By means of the fixing device, the circumference of the inner surface and thus also the diameter of the inner surface of the centring bush can therefore be reduced, with the result that a force acting radially inwards is applied to the first eccentric bush. Through the friction generated thereby between the inner surface of the centring bush and the centring outer surface of the first eccentric bush, these are fixed relative to each other. If the second eccentric bush is also arranged in such a way that it is introduced in the axial direction into the first eccentric bush such that it is arranged at the axial height of the centring bush, then the fixing device can fix not only the position of the first eccentric bush relative to the centring bush but also the position of the second eccentric bush relative to the first eccentric bush and the centring bush. This is achieved in particular when the first eccentric bush comprises the compensating section since then the radial force can be transferred particularly well because of the alterable circumference of the first eccentric bush. By reducing the circumference of the inner surface of the centring bush, the frictional force between the centring bush and the first eccentric bush and/or between the first eccentric bush and the second eccentric bush increases, with the result that it is no longer possible to rotate the first eccentric bush relative to the centring bush and/or the second eccentric bush.

In order to be able to reduce the circumference of the inner surface of the centring bush particularly simply, the centring bush comprises at least one gap running along the direction of the axis of rotation. The gap preferably has the properties of the slot in the first eccentric bush and/or the second eccentric bush. For example, the centring bush can comprise a base ring and two, three, four or more tongues which protrude from the base ring in the direction of the axis of rotation and are each separated from each other in the circumferential direction by the gap, and the inner surfaces of which mount the first eccentric bush rotatably about the axis of rotation.

In order to alter the inner circumference of the first centring bush particularly simply it is preferred that the fixing device comprises at least one circular wedge, in particular three circular wedges, and the centring bush comprises at least one corresponding circular wedge, in particular three corresponding circular wedges. Depending on the design, a turning moment can be applied to the centring bush in the axial and/or radial direction by means of the circular wedge. The circular wedge of the fixing device optionally protrudes in the direction of the centre or of the axis of rotation of the centring bush and further optionally is a segment of an Archimedean spiral. The circular wedge of the centring bush is arranged opposite the circular wedge of the fixing device, for example on a circumferential surface of the centring bush, in particular on the tongues, and formed corresponding to the circular wedge of the fixing device. The use of three circular wedges has proved to be particularly advantageous in order to form a 3-component clamping bush. By rotating the fixing device in the direction of the centre of the Archimedean spiral of the circular wedge, self-locking forms between the centring bush and the fixing device. The fixing device can also be called a clamping bush.

In another variant, the fixing device can comprise a thread, in particular a conical thread. In this case, the centring bush can comprise a matching thread on its outside, with the result that, by turning the centring bush, the latter can be clamped or locked relative to the first eccentric bush and/or the second eccentric bush. In this case, the fixing device can be formed as a lock nut.

The disclosure further includes a method for centring an eyepiece in a main unit of an endoscope, wherein the main unit comprises a proximal end and, at the proximal end, comprises a centring bush with an inner surface which defines an axis of rotation. A first eccentric bush is provided, which is mounted rotatable about the axis of rotation in the centring bush at the proximal end and comprises a first centring inner surface, which defines a first rotation axis, wherein the first rotation axis is offset parallel to the axis of rotation by a first offset. Furthermore, a second eccentric bush is provided which is mounted rotatable about the first rotation axis in the first eccentric bush and comprises a second centring inner surface, which defines a second rotation axis, wherein the second rotation axis is offset parallel to the first rotation axis by a second offset. The eyepiece, which has an optical axis which is parallel to the second rotation axis, is connected to the second eccentric bush. By rotating the first eccentric bush and/or the second eccentric bush the eyepiece is offset radially with respect to the axis of rotation until the optical axis coincides with the axis of rotation.

The considerations, preferred embodiments, variants and developments made with respect to the endoscope apply analogously to the method.

The invention also includes an eyepiece centring mechanism for a main unit of an endoscope, as has been described above.

It is understood that the features named above and those yet to be explained below can be used not only in the stated combinations but also in other combinations or alone, without departing from the scope of the present invention.

Figure 1:
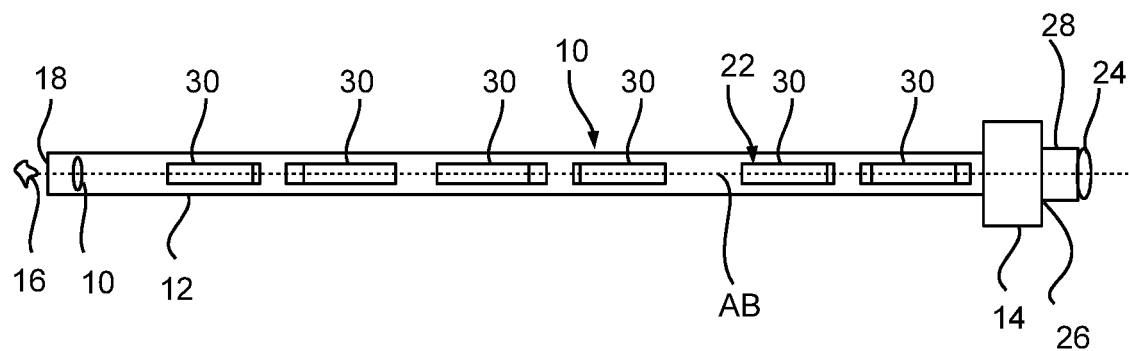
FIG. 1 is a schematic representation of an endoscope.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

An endoscope 10 according to the invention according to the embodiment shown in FIG. 1 comprises a shaft 12 and a main unit 14. An object 16 which is located, for example, in a body cavity can be observed with the endoscope 10. For this purpose, a distal end 18 of the endoscope 10, in particular the distal end 18 of the shaft 12, is inserted into the body cavity. The object 16 is presented to a user via an objective lens 20, which is provided at the distal end 18 of the shaft 12, via an optical guidance system 22 and an eyepiece 24. The eyepiece 24 is provided at a proximal end 26 of the main unit 14; in particular, the eyepiece 24 is arranged at the distal end 18 of the main unit 14 via an eyepiece centring mechanism 28 according to the invention. The optical guidance system 22 can be composed, for example, of several lenses 30, in particular rod-shaped lenses 30, or of a light guide system. The objective lens 20 and the optical guidance system 22 determine an imaging axis AB, which represents a centre axis for the imaging of the object 16.

The eyepiece 24 has an optical axis OA. The eyepiece 24 can comprise one or more lenses which can be shifted, for example, relative to each other (along the optical axis OA, for example) in order to alter the imaging properties of the eyepiece 24. The imaging axis AB is determined by the main unit 14 and the shaft 12. In order to enable or to improve an imaging of the object 16, the optical axis OA of the eyepiece 24 should coincide with the imaging axis AB. The eyepiece centring mechanism 28 is provided for parallel shifting of the optical axis OA of the eyepiece 24. It can be used to shift the optical axis OA parallel in a radial direction.

The eyepiece centring mechanism 28 comprises a centring bush 32, a first eccentric bush 34, a second eccentric bush 36 and a fixing device 38. As can be seen in particular in FIGS. 2 and 3, the centring bush 32 is connected to the main unit 14 (it can also be formed in one piece with the main unit 14). The centring bush 32 optionally comprises a base ring 40 and several tongues 42. The base ring 40 represents the connection of the tongues 42 to the main unit 14. The tongues 42 protrude from the base ring 40 along an axis of rotation RA of the centring bush 32. The axis of rotation RA coincides, for example, with the imaging axis AB. The tongues 42 are separated from each other in each case by a gap 44; the gaps 44 extend in each case in the direction of the axis of rotation RA. Because of the gaps 44, the centring bush 32 can be deformed radially inwards in the area of the tongues 42, in particular in that the tongues 42 are bent inwards in comparison with the base ring 40.

The centring bush 32 comprises an inner surface 46 which is defined, for example, by the tongues 42. A diameter of the inner surface 46 can be reduced through the deformability of the tongues 42. The inner surface 46 is optionally shaped in such a way that a cylinder can be mounted rotatable about the axis of rotation RA on the inner surface 46. For this purpose, on the inner surface 46 the tongues 42 are formed, for example, in cross section perpendicular to the axis of rotation RA, like circular segments, the centre of which lies on the axis of rotation RA. Furthermore, the tongues 42 can be formed like segments of a thin-walled hollow cylinder, wherein the axis of symmetry of the hollow cylinder coincides with the axis of rotation RA. The centring bush 32 comprises three circular wedges 74 on its outside; one for each tongue 42. The radius of an outer surface of the circular wedges 74 increases in the circumferential direction, for example like an Archimedean spiral.

The first eccentric bush 34 comprises a first centring section 48 and a first collar 50. The first eccentric bush 34 is mounted rotatable about the axis of rotation RA in the centring bush 32. For this purpose, the first centring section 48 is pushed into the centring bush 32 for example and abuts against the inner surface 46, while the first collar 50 forms a limit stop in the direction of the axis of rotation RA. The axis of rotation RA defines an axial direction of the eyepiece centring mechanism 28.

The first eccentric bush 34 comprises a first compensating section 52, which extends completely through the first eccentric bush 34 in the direction of the axis of rotation RA. In the embodiment shown, the first compensating section 52 is formed as a slot. The first compensating section 52 enables an outer circumference of the first eccentric bush 34 and thus also an inner circumference of the first eccentric bush 34 to be altered by bringing the ends of the first eccentric bush 34 which are opposite the first compensating section 52 closer together.

The first eccentric bush 34 further comprises a first centring outer surface 54 and a first centring inner surface 56. The first centring outer surface 54 can be formed, for example, by a lateral surface of the first centring section 48. Likewise, the first centring inner surface 56 can be formed by the first centring section 48. The first centring outer surface 54 is formed in such a way that it can be mounted rotatable about the axis of rotation RA in a hollow cylinder. For this purpose, the first centring section 48 can be designed like a hollow cylinder, for example.

Figure 4:
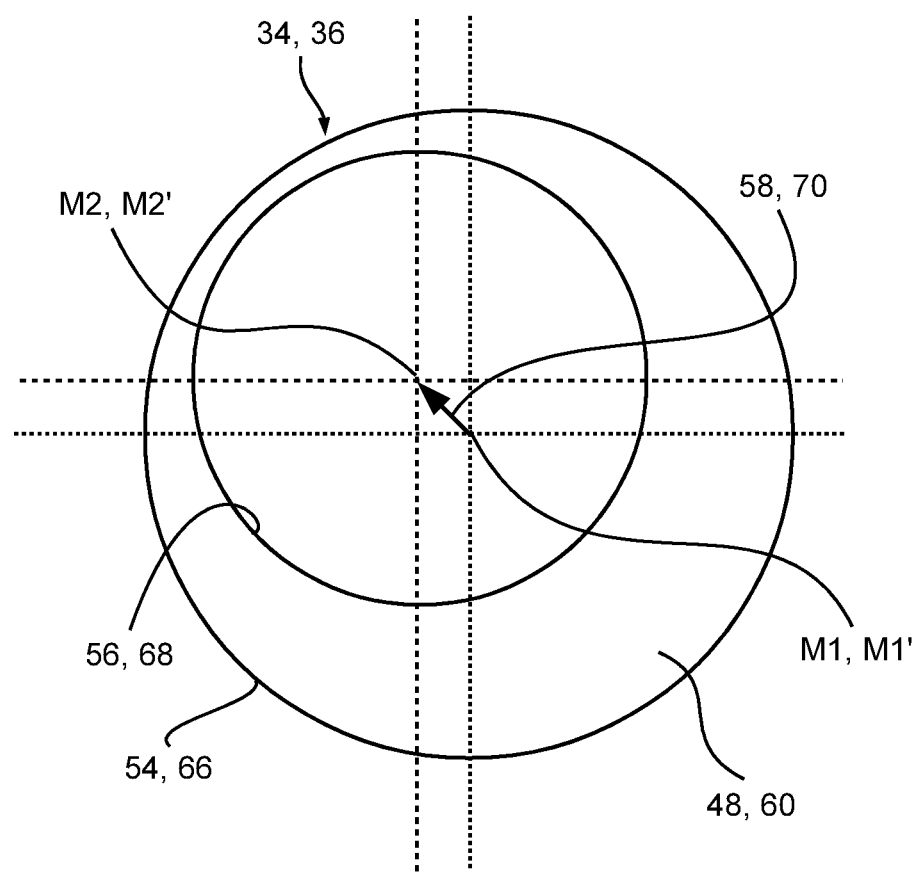
FIG. 4 is a cross-sectional view of an eccentric bush of the eyepiece centring mechanism from FIG. 4.

The first centring inner surface 56 defines a first rotation axis D1. The first centring inner surface 56 is formed in such a way that a cylinder can be mounted rotatable about the first rotation axis D1. For this purpose, the first centring inner surface 56 can be formed like the inner wall of a hollow cylinder, wherein the first compensating section 52 is provided in the form of a slot. As can be seen in particular in FIG. 4, the first centring inner surface 56 can be formed in cross section like a circle which has a first centre M1. The first centring outer surface 54 can likewise be formed in cross section like a circle which has the second centre M2. The first centre M1 lies on the axis of rotation RA, while the second centre M2 lies on the first rotation axis D1. The axis of rotation RA is offset relative to the first rotation axis D1 by a first offset 58. The first offset 58 indicates the direction and the length of the offset. The first offset 58 therefore determines an eccentricity of the first eccentric bush 34. The first offset 58 in particular points in the direction of the first compensating section 52. In FIG. 4 the first offset is represented disproportionately large, wherein the first compensating section 52 has not been represented in FIG. 4.

Figure 2:
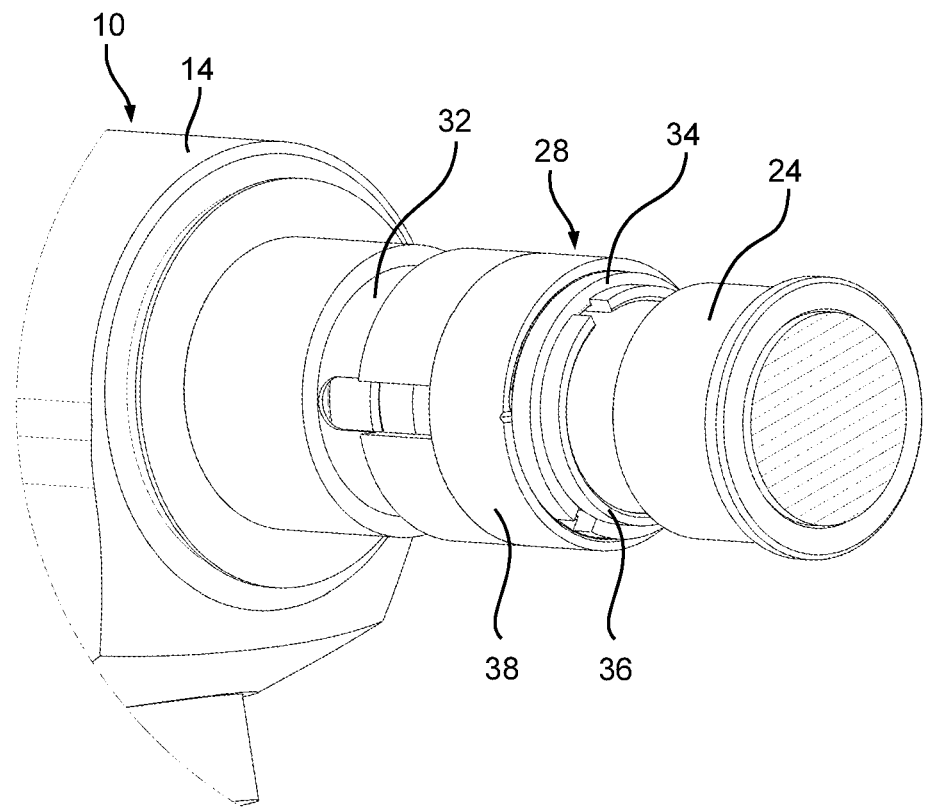
FIG. 2 is a schematic representation of a main unit and of an eyepiece centring mechanism of the endoscope from FIG. 1.
Figure 3:
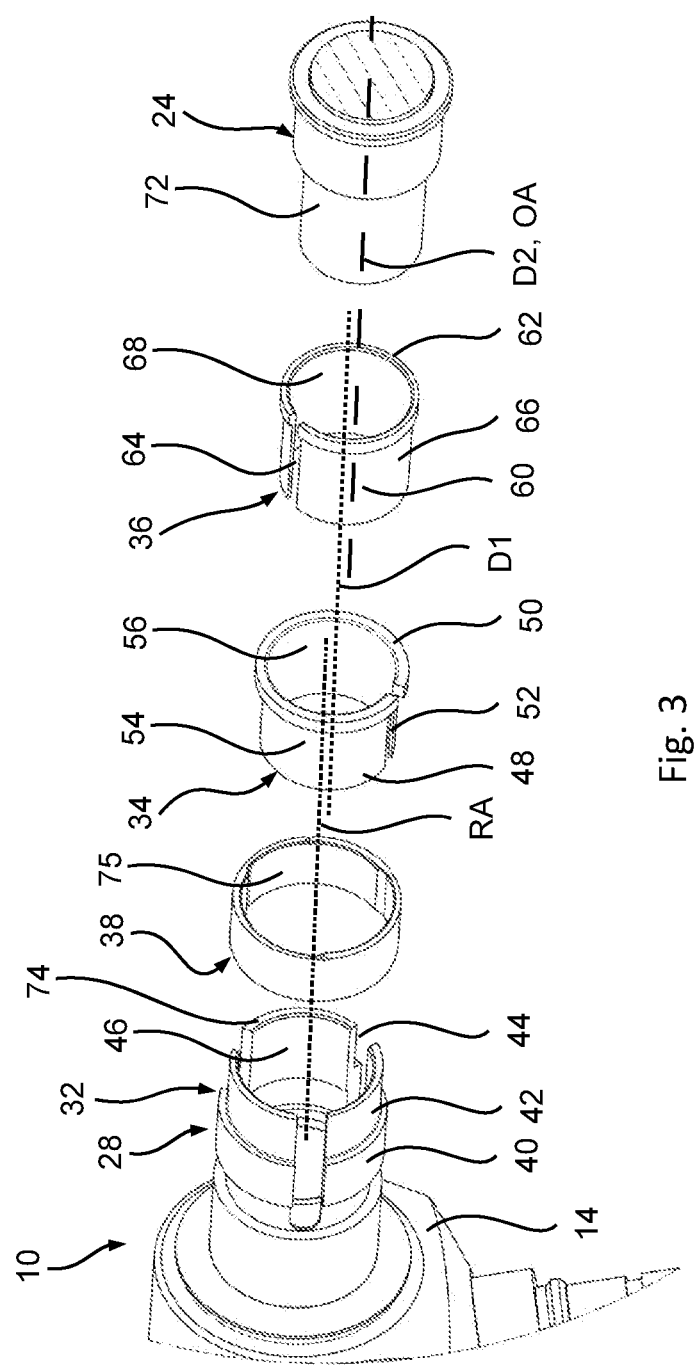
FIG. 3 is a schematic exploded representation of the main unit and of the eyepiece centring mechanism according to FIG. 2.

As can be seen, e.g., in FIG. 2, the second eccentric bush 36 comprises a second centring section 60 and a second collar 62. The second eccentric bush 36 is mounted rotatable about the first rotation axis D1 in the first eccentric bush 34. For this purpose, the second centring section 60 is pushed into the first eccentric bush 34 for example and abuts against the first centring inner surface 56, while the second collar 62 forms a limit stop in the direction of the first rotation axis D1.

The second eccentric bush 36 comprises a second compensating section 64, which extends completely through the second eccentric bush 36 in the direction of a second rotation axis D2 of the second eccentric bush 36. In the embodiment shown, the second compensating section 64 is formed as a slot. The second compensating section 64 enables an outer circumference of the second eccentric bush 36 and thus also an inner circumference of the second eccentric bush 36 to be altered, in particular reduced, by bringing the ends of the second eccentric bush 36 which are opposite the second compensating section 64 closer together.

The second eccentric bush 36 further comprises a second centring outer surface 66 and a second centring inner surface 68. The second centring outer surface 66 can be formed, for example, by a lateral surface of the second centring section 60. Likewise, the second centring inner surface 68 can be formed by the second centring section 60. The second centring outer surface 66 is formed in such a way that it can be mounted rotatable about the first rotation axis D1 in a hollow cylinder. For this purpose, the second centring section 60 can be designed like a hollow cylinder, for example.

The second centring inner surface 68 defines the second rotation axis D2. The second centring inner surface 68 is formed in such a way that a cylinder can be mounted rotatable about the second rotation axis D2. The second rotation axis D2 is arranged parallel to the first rotation axis D1 and the axis of rotation RA. For this purpose, the second centring inner surface 68 can be formed like the inner wall of a hollow cylinder, wherein the second compensating section 64 is provided in the form of a slot. The second centring inner surface 68 is designed in cross section analogously to the first centring inner surface 56 represented in FIG. 4. The second centring inner surface 68 can be formed in cross section like a circle which has a first centre Mr. The second centring outer surface 66 can likewise be formed in cross section like a circle which has the second centre M2'. The first centre M1' lies on the first rotation axis D1, while the second centre M2' lies on the second rotation axis D2. The second rotation axis D2 is offset relative to the first rotation axis D1 by a second offset 70. The second offset 70 indicates the direction and the length of the offset. The second offset 70 therefore determines an eccentricity of the second eccentric bush 36.

The first offset 58 and the second offset 70 can be formed identical, in particular the lengths of the first and second offsets 58, 70 are identical.

The eyepiece 24 is connected to the second eccentric bush 36. For this purpose, the eyepiece 24 can comprise, for example, an insertion section 72, which is pushed into the second eccentric bush 36. The optical axis OA of the eyepiece 24 coincides with the second rotation axis D2.

Figure 5:
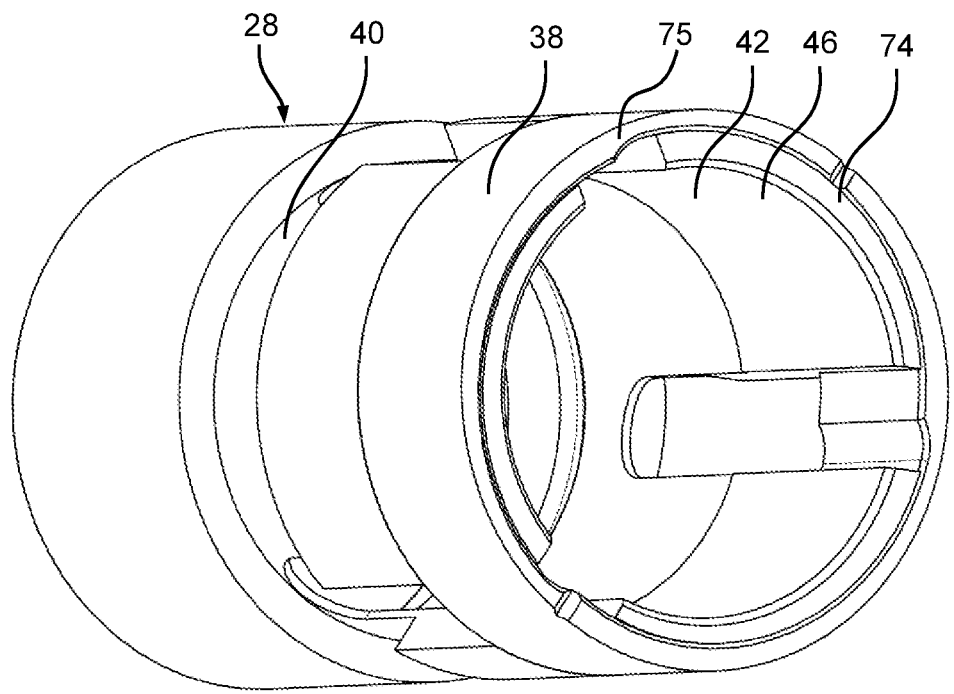
FIG. 5 is a perspective representation of the eyepiece centring mechanism without eyepiece from FIG. 3.
Figure 6:
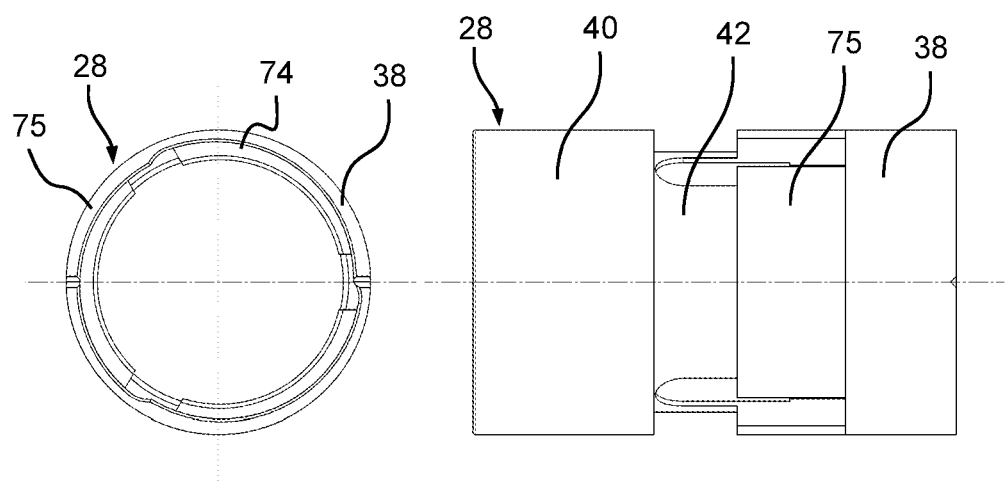
FIG. 6 is a cross-sectional view and a side view of a centring bush and of a fixing device of the eyepiece centring mechanism according to FIG. 5.

The fixing device 38 is provided to hold the eyepiece 24 in place in the second eccentric bush 36, to hold the second eccentric bush 36 in place in the first eccentric bush 34 and to hold the first eccentric bush 34 in place in the centring bush 32. This is located on an outer surface of the centring bush 32 and is used to reduce the size of a diameter of the inner surface 46 of the centring bush 32, in particular of the tongues 42. For this purpose, the fixing device 38 comprises, on its inside, at least one circular wedge 75, in particular three circular wedges 75. The circular wedges 75 are arranged like segments of an Archimedean spiral, as can be seen in FIGS. 5 and 6, and in particular are formed evenly around the circumference of the fixing device 38. By rotating the fixing device 38 relative to the centring bush 32, a turning moment forms because of the circular wedges 74 and 75, which acts axially and radially on the centring bush 32. The centring bush 32, in particular the tongues 42 thereof, is deformed radially inwards, with the result that a frictional connection forms between the centring bush 32 and first eccentric bush 34 because of the reduction in the diameter of the inner surface 46 caused thereby at the points at which the circular wedges 74, 75 touch. Since the first compensating section 52 is provided in the first eccentric bush 34, the turning moment generated by the turning of the fixing device 38 can be transferred from the centring bush 32 to the first eccentric bush 34 and thus also to the second eccentric bush 36. The circumference of the first eccentric bush 34 is thus alterable, whereby a frictional connection forms between the first eccentric bush 34 and the second eccentric bush 36. Since the outer circumference of the second eccentric bush 36 can also be alterable using the second compensating section 64, a frictional connection is also formed between the second eccentric bush 36 and the eyepiece 24. The eyepiece 24 is thus held in place relative to the centring bush 32.

However, the fixing device 38 can also be formed as a nut which can be screwed onto the centring bush 32 by means of a thread.

Figure 7:
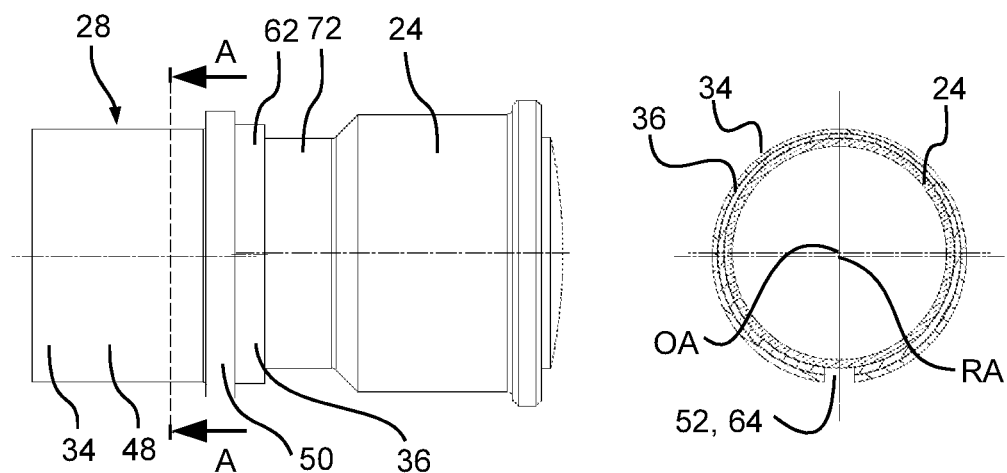
FIG. 7 is a cross-sectional view as well as a side view along the line A-A of the eyepiece centring mechanism from FIG. 2.
Figure 8:
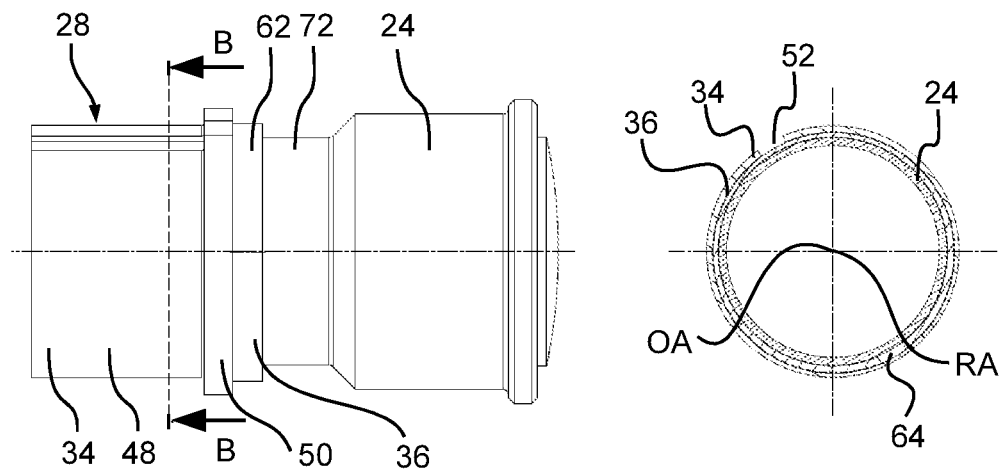
FIG. 8 is a schematic side view and a cross-sectional view along the line B-B of the side view in a further rotational position shown in comparison with FIG. 7.

In order to alter the optical axis OA of the eyepiece 24 relative to the imaging axis AB or the axis of rotation RA, the first eccentric bush 34 and/or the second eccentric bush 36 are rotated along their circumference. Because of the first offset 58 and the second offset 70, the optical axis OA can be offset parallel relative to the axis of rotation RA, as is shown in FIG. 7. The turning of the first and/or second eccentric bush 34, 36 leads to the respective rotation axis D1, D2 being displaced relative to the respective centring outer surface 54, 66 in the direction of the offset. If the first offset 58 is arranged mirror-inverted relative to the second offset 70, the axis of rotation RA is located identically to the optical axis OA, as is shown in FIG. 8.

The position of the first offset 58 and/or of the second offset 70 can optionally be recognized by markings. An example of such a marking is the first compensating section 52 and/or the second compensating section 64. These are arranged as marking such that an imaginary extension of the first offset 58 intersects the first compensating section 52 and/or an imaginary extension of the second offset 70 intersects the second compensating section 64. In this way, the position of the first compensating section 52 and/or of the second compensating section 64 indicates the direction of the respective offset 58, 70.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. An endoscope, comprising
a main unit comprising a proximal end and including at the proximal end a centring bush with an inner lumen having a first central longitudinal axis;
a first eccentric bush, a portion of which is nested within the inner lumen of the centring bush, with an inner lumen having a second central longitudinal axis, wherein the first central longitudinal axis is offset parallel to the second central longitudinal axis;
a second eccentric bush, a portion of which is nested within the inner lumen of the first eccentric bush, with an inner lumen having a third central longitudinal axis, wherein the second central longitudinal axis is offset parallel to the third central longitudinal axis; and
an eyepiece, a portion of which is nested within the inner lumen of the second eccentric bush, and has an optical axis that is parallel to the third central longitudinal axis, wherein an amount of optical axis offset with respect to the first central longitudinal axis is adjustable by rotating at least one of the first eccentric bush and the second eccentric bush.

2. The endoscope according to claim 1, wherein the first eccentric bush comprises a first hollow cylinder and the second eccentric comprises a second hollow cylinder, wherein each of the first and second hollow cylinders includes a compensating section, and wherein each of the compensating sections extend in the direction of the respective central longitudinal axis and are alterable in their extent in order to alter an outer circumference of the respective first and second hollow cylinders.

3. The endoscope according to claim 2, wherein each of the compensating sections comprises a slot.

4. The endoscope according to claim 3, wherein at least one of an imaginary extension in the direction of the first offset intersects the compensating section of the first eccentric bush and an imaginary extension of the second offset intersects the compensating section of the second eccentric bush.

5. The endoscope according to claim 2, wherein at least one of an imaginary extension in the direction of the first offset intersects the compensating section of the first eccentric bush and an imaginary extension of the second offset intersects the compensating section of the second eccentric bush.

6. The endoscope according to claim 1, wherein a length of the first offset is equal to a length of the second offset.

7. The endoscope according to claim 1, wherein a diameter of the inner lumen of the centring bush can be reduced in order to hold the centring bush in place by means of frictional connection through a fixing device.

8. The endoscope according to claim 7, wherein the centring bush has at least one gap.

9. The endoscope according to claim 8, wherein the fixing device comprises at least one circular wedge and the centring bush comprises at least one corresponding circular wedge.

10. The endoscope according to claim 8, wherein the fixing device comprises at least three circular wedges and the centring bush comprises at least three corresponding circular wedges.

11. The endoscope according to claim 8, wherein the fixing device comprises a thread.

12. The endoscope according to claim 11, wherein the thread is a conical thread.

13. The endoscope according to claim 7, wherein the fixing device comprises at least one circular wedge and the centring bush comprises at least one corresponding circular wedge.

14. The endoscope according to claim 7, wherein the fixing device comprises at least three circular wedges and the centring bush comprises at least three corresponding circular wedges.

15. The endoscope according to claim 7, wherein the fixing device comprises a thread.

16. The endoscope according to claim 15, wherein the thread is a conical thread.

* * * * *